United States Patent [19]

Illi

[11] Patent Number: 5,601,603
[45] Date of Patent: Feb. 11, 1997

[54] USE OF AND PROCESS FOR THE INTRODUCTION OF FIBRIN SEALANT INTO A PUNCTURE CHANNEL

[75] Inventor: Oskar Illi, Schwerzenbach, Switzerland

[73] Assignee: White Spot AG, Switzerland

[21] Appl. No.: 387,728

[22] PCT Filed: Jun. 9, 1994

[86] PCT No.: PCT/CH94/00114

§ 371 Date: Feb. 16, 1995

§ 102(e) Date: Feb. 16, 1995

[87] PCT Pub. No.: WO94/28798

PCT Pub. Date: Dec. 22, 1994

[30] Foreign Application Priority Data

Jun. 16, 1993 [CH] Switzerland .............. 1792/93

[51] Int. Cl.⁶ ........................................ A61B 17/00
[52] U.S. Cl. .............. 606/213; 604/12; 604/73; 604/82; 604/164; 604/264; 604/280
[58] Field of Search .................. 606/213, 214, 606/1; 604/164, 181, 257, 275, 264, 280, 270, 73, 12, 39, 40, 43, 46, 82, 83, 89

[56] References Cited

U.S. PATENT DOCUMENTS

| | | |
|---|---|---|
| 1,882,213 | 10/1932 | Donovan . |
| 2,589,388 | 3/1952 | Hunter ........................ 604/275 |
| 4,563,180 | 1/1986 | Jervis et al. ................. 604/280 |
| 4,897,079 | 1/1990 | Zaleski et al. ................. 604/43 |
| 4,904,238 | 2/1990 | Williams ........................ 604/43 |
| 4,935,006 | 6/1990 | Hasson ........................... 604/43 |
| 4,959,058 | 9/1990 | Michelson ..................... 604/280 |
| 5,300,032 | 4/1994 | Hibbs et al. .................. 604/164 |

FOREIGN PATENT DOCUMENTS

| | | |
|---|---|---|
| 0241038 | 10/1987 | European Pat. Off. . |
| 0443256 | 8/1991 | European Pat. Off. . |
| 0482350 | 4/1992 | European Pat. Off. . |
| 2378528 | 8/1978 | France . |
| 0286145 | 11/1970 | U.S.S.R. ........................ 604/43 |

*Primary Examiner*—Jeffrey A. Schmidt
*Attorney, Agent, or Firm*—Speckman, Pauley & Fejer

[57] ABSTRACT

A device for introducing a two-component fibrin sealant into a puncture channel in the vicinity of an arterial or venous puncture point, said device comprising a working cannula extending axially from an upper end to a lower end through a sealing cannula, said working cannula being used for intravascular introduction of instruments into a vessel. The working cannula is surrounded by the sealing cannula at a distance from the working cannula whereby the fibrin sealant passes from a connector at said upper end of said sealing cannula to at least one slitshaped radially directed outlet opening in said sealing cannula between said sealing cannula and said working cannula.

12 Claims, 4 Drawing Sheets

USE OF AND PROCESS FOR THE INTRODUCTION OF FIBRIN SEALANT INTO A PUNCTURE CHANNEL

BACKGROUND OF THE INVENTION

1. Field of the Invention

This invention relates to the use of endogenous blood coagulants obtained from plasma protein in the form of a two-component fibrin sealant, said components being mixed at the instant they are delivered.

This invention also relates to a device for introducing the two-component fibrin sealant into a puncture channel in the vicinity of an arterial or venous puncture point.

2. Description of Prior Art

Many operations in human or veterinary medicine require puncturing of vessels. With percutaneous transluminar coronary angioplasty (PTCA), heart operations and catheterizations of the heart, in particular, it is necessary to close the punctured vessels again with great care. In most cases, this is performed by direct compression of up to one hour and a compression bandage which must be applied up to 24 hours and requires hospitalization of one to two days. Accordingly, there is the desire to find a means for a more rapid and secure closure of the puncture point.

A method by the name of Vasoseal was introduced during a meeting of the American Heart Association on 17 Nov. 1992 in New Orleans. In accordance with this method, two collagen plugs made of bovine collagen are pushed into the puncture channel as far as the puncture point. It was noted during the meeting that, besides the somewhat rare rejection reaction of the exogenous collagen, there are various other disadvantages or risks. It was also noted that this system is ineffective in many cases and that there is a certain danger of emboli. In approximately 46% of all cases, hematomas of an order of magnitude between 2 to 6 cm were formed. Weeks or months go by before the bovine collagen is completely resorbed. In addition, the method leads to increased scar formation which makes an ultrasonic examination more difficult. Finally, although hospitalization did not become superfluous, it was reduced by at least 24 hours. However, one of the most essential problems lies in the handling, that is, the introduction of the collagen plugs into the puncture channel. Because it is necessary to push two collagen plugs successively into the puncture channel, the user finds the penetration depth, for example, hard to determine. If the collagen plugs are pushed in too deeply, the collagen plug may be pushed through the puncture point into the vessel, resulting in an obstruction in the vessel or the vessel itself being pushed closed.

SUMMARY OF THE INVENTION

Accordingly, it is an object of this invention to provide a novel method for closing such puncture points rapidly, dependably and without the above mentioned disadvantages.

It has been shown that when endogenous blood coagulants obtained from plasma protein in the form of a two-component fibrin sealant, whose components are mixed at the instant they are delivered, are used, and this mixture is introduced into a puncture channel as close as possible to a vessel during or directly following an intravascular intervention, an optimal vessel seal is created. Histological tests have proven these facts.

It is a further object of this invention to provide a device by which fibrin sealant can be introduced into a puncture channel in the vicinity of an arterial or venous puncture point.

These and other objects are attained by a device in accordance with one embodiment of this invention comprising a sealing cannula through which a work cannula passes axially from top to bottom, wherein the work cannula which is used for the intravascular introduction of an instrument into a vessel is surrounded at a distance by the sealing cannula, so that the fibrin sealant is conducted between the sealing cannula and the work cannula from a connector to at least one radially oriented outlet opening in the sealing cannula.

BRIEF DESCRIPTION OF THE DRAWINGS

These and other features and objects of this invention will be better understood from the following detailed description taken in conjunction with the drawings wherein.

DESCRIPTION OF PREFERRED EMBODIMENTS

Figure 1:
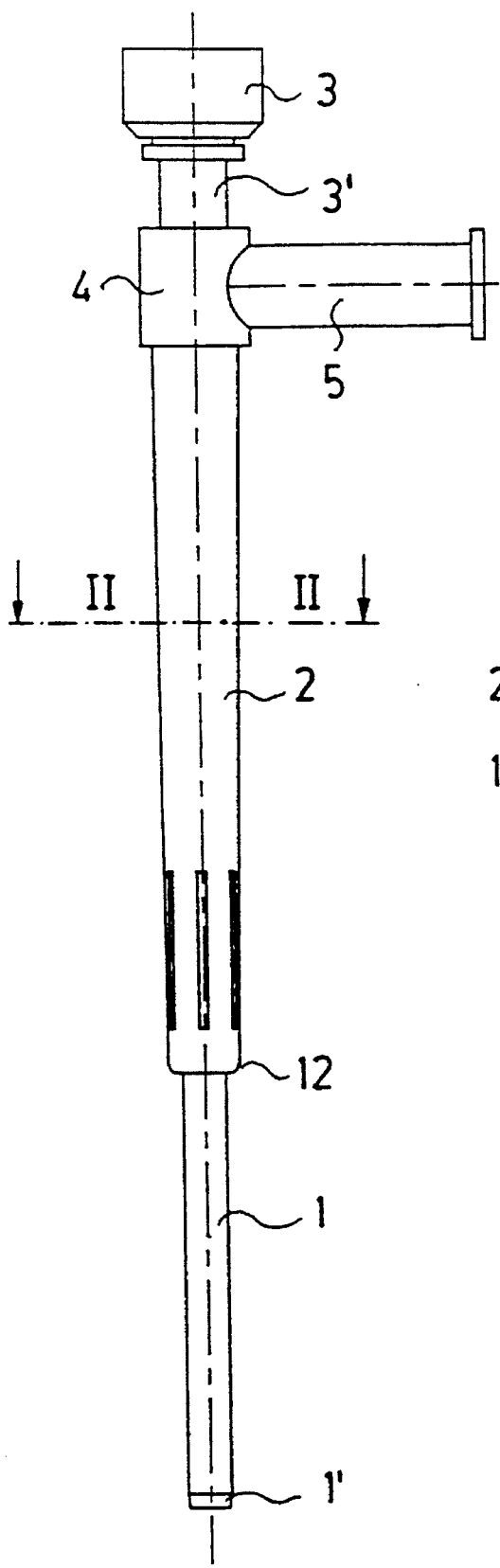
FIG. 1 is a side view of the device in accordance with one embodiment of this invention.
Figure 2:
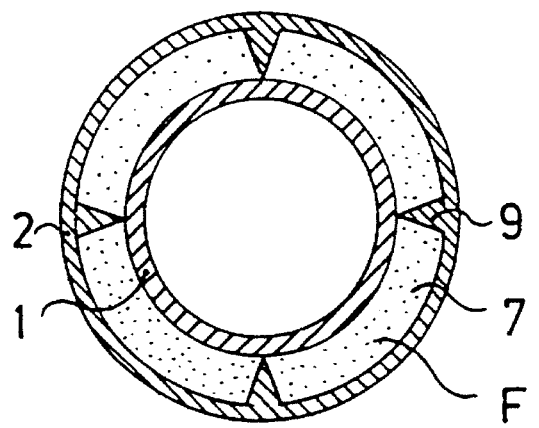
FIG. 2 is a cross sectional view through the device of FIG. 1 along the line II—II on an enlarged scale.
Figure 3:
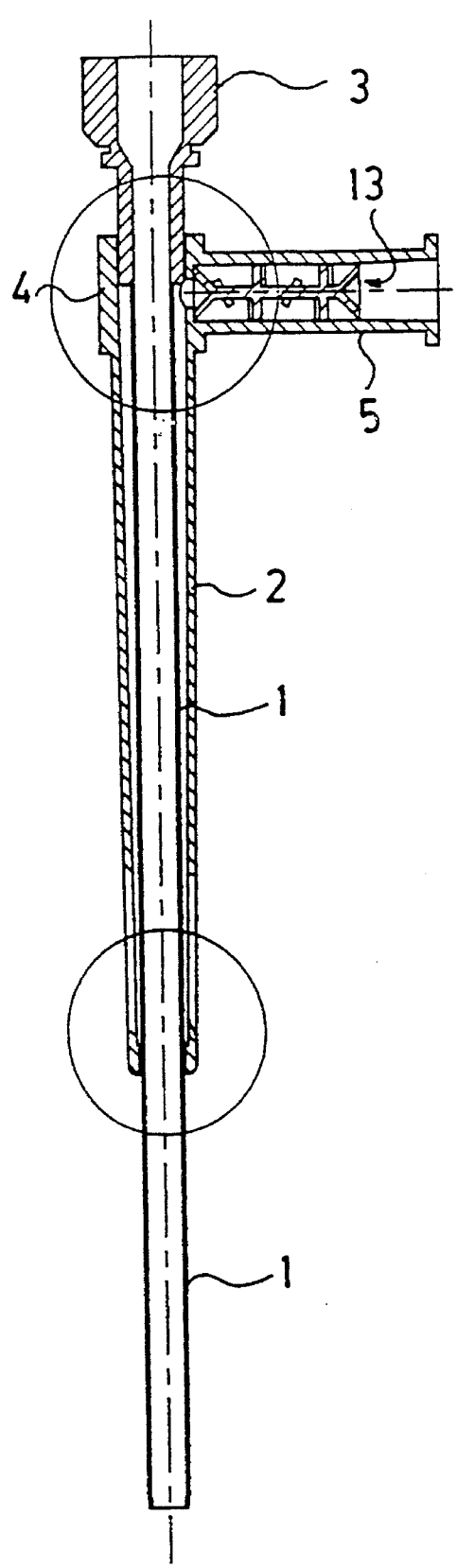
FIG. 3 is a longitudinal cross sectional view of the device shown in FIG. 1.
Figure 4:
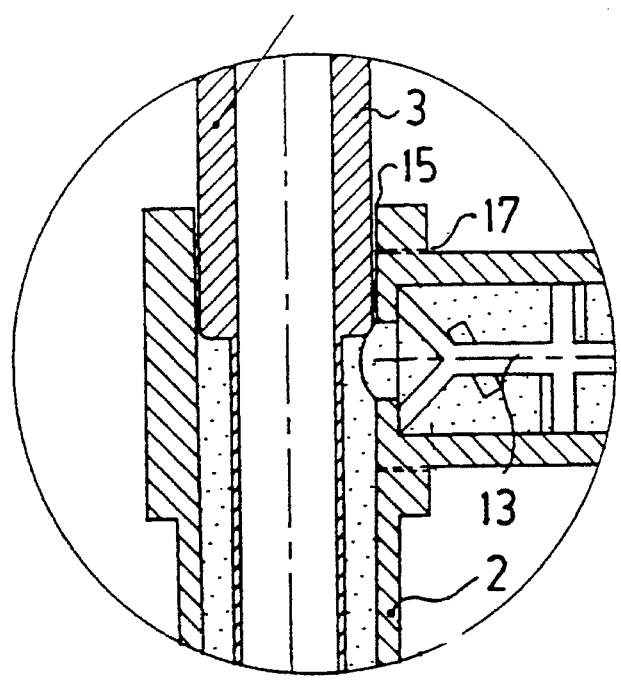
FIG. 4 is an enlarged cross sectional view of the connector area of the device in accordance with one embodiment of this invention.
Figure 5:
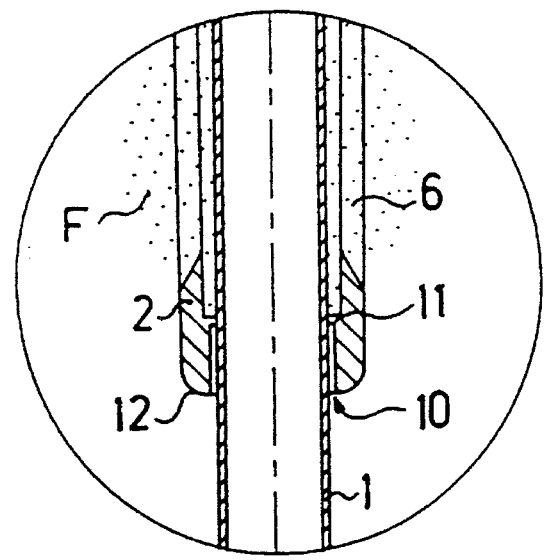
FIG. 5 is an enlarged longitudinal cross sectional view of the exit area of the working cannula from the sealing cannula in accordance with one embodiment of this invention.

In what follows, two preferred embodiments of the device of this invention and then their manipulation and the general employment of fibrin sealant for sealing a puncture point in a vessel will be described. The embodiment of the device of this invention in accordance with FIGS. 1 to 5 comprises only three elements which can be put together. The working cannula, also called worksheath in technical language, is identified by the reference numeral 1. The working cannula itself is a small cylindrical tube, open at both ends, made of plastic. Its front end 1' is used for introducing the cannula through the puncture point into the opened blood vessel. The working cannula is relatively thin-walled and therefore has a certain amount of bending flexibility. In accordance with this embodiment of the device of this invention, the working cannula 1 is fixedly connected to a medical coupling 3 at the other end, the rear end. The actual medical coupling 3 can be a known Luer locking coupling, for example. An exactly fashioned muff 3' is formed in an interlocking and sealing manner on the actual medical coupling 3. The working cannula 1 axially extends in the longitudinal direction through a sealing cannula 2 and, at the front end, projects for some distance out of the sealing cannula. The sealing cannula 2 itself is also embodied as a small concentric tube, but its exterior diameter, and preferably also its interior diameter, decrease from the top end to the bottom end, that is, the interior diameter is reduced from the top end where the medical coupling 3 is inserted to the bottom end where the working cannula 1 emerges from the sealing cannula 2.

Thus, a hollow space 7 is formed between the working cannula 1 and the sealing cannula 2 over the entire length where the working cannula 1 is concentrically enclosed by the sealing cannula 2. The sealing cannula 2 has a reinforced cuff 4 at the top end which has a considerably greater wall thickness than the wall thickness of the sealing cannula 2. A connector 5 terminates in the sealing cannula 2 in the area of the reinforced cuff 4. A two-component fibrin sealant (F) is introduced into the hollow space between the working cannula 1 and the sealing cannula 2 through this connector 5. The fibrin sealant exits from the hollow space 7 only through the at least one outlet opening 6 in the lower area of the sealing cannula 2. So that fibrin sealant does not unintentionally enter the blood vessel, the at least one outlet opening 6 is at least approximately radially oriented toward the outside. By radially, not only the direction, interpreted in a strictly geometric sense, is meant. Rather this is only intended to express that the outflow direction is not axial. The functioning of the device is assured by a single outlet opening, but preferably several outlet openings 6 distributed over the circumference may be provided. Also, in principle, the form of the embodiment of the outlet openings 6 can be freely designed. However, for technical production reasons, they are preferably formed in the shape of several linear slits distributed over the circumference.

To form an exact receptacle 15 for the medical coupling 3, the upper opening of the sealing cannula 2 must be provided with a snug fit.

For sealing the working cannula 1 against the sealing cannula 2 in the area of the through-opening 10, an annular sealing bead or sealing rib 11, which is oriented radially inward and sealingly rests on the outer surface of the working cannula 1, is disposed in the through-opening 10.

In accordance with a preferred embodiment of this invention, the connector 5 is formed in one piece directly on the sealing cannula 2 in the area of the reinforced cuff. It is, however, possible to manufacture the connector separately and to connect it later with the sealing cannula by a screw connection 17. In place of the screw connection 17, a welded or adhesive connection is also possible. Mixing elements are already available on the market for mixing the two components of the two-component fibrin sealant. Therefore, for reasons of cost, the connector 5 should be sized such that an already available mixing element 13 can be inserted into it.

As already mentioned, the wall thickness of the working cannula 1 is very little. Preferably, it is only a few tenths of a millimeter. The hollow space 7 remaining concentrically around the working cannula 1 between its outer wall and the inner wall of the sealing cannula 2 is of extremely small dimensions. Because all of the surgical instruments must be inserted and removed though the working cannula 1, it is preferred to provide means which enable the hollow space 7 to remain continuously open. Support ribs 9 which preferably extend axially are disposed on the inner wall of the sealing cannula 2 for this purpose.

Figure 7:
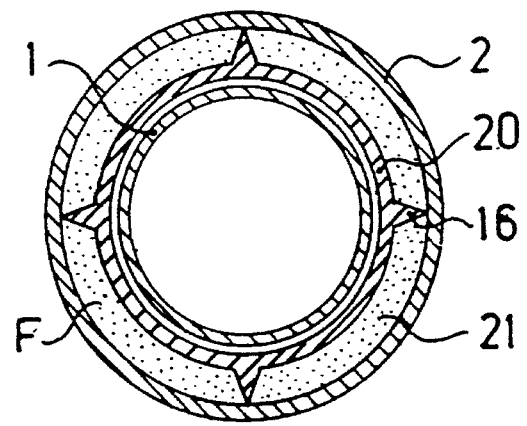
FIG. 7 is a cross sectional view through the device of FIG. 6 along the line VII—VII.
Figure 6:
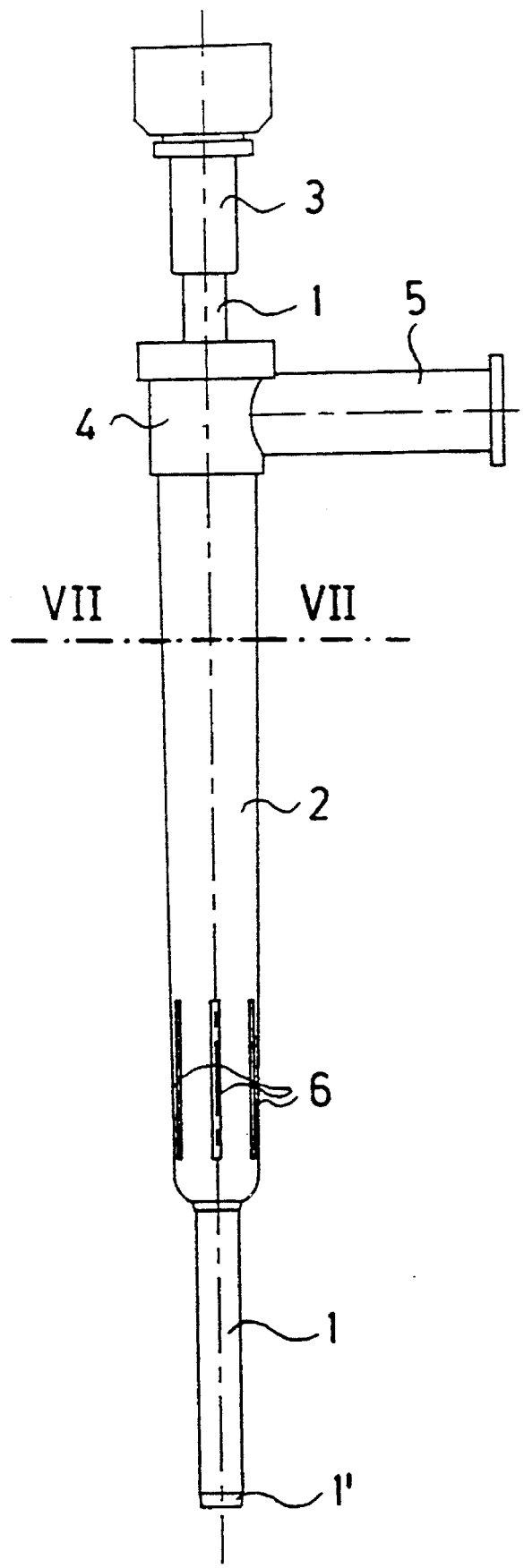
FIG. 6 shows a side view of a second embodiment of the device of this invention.
Figure 8:
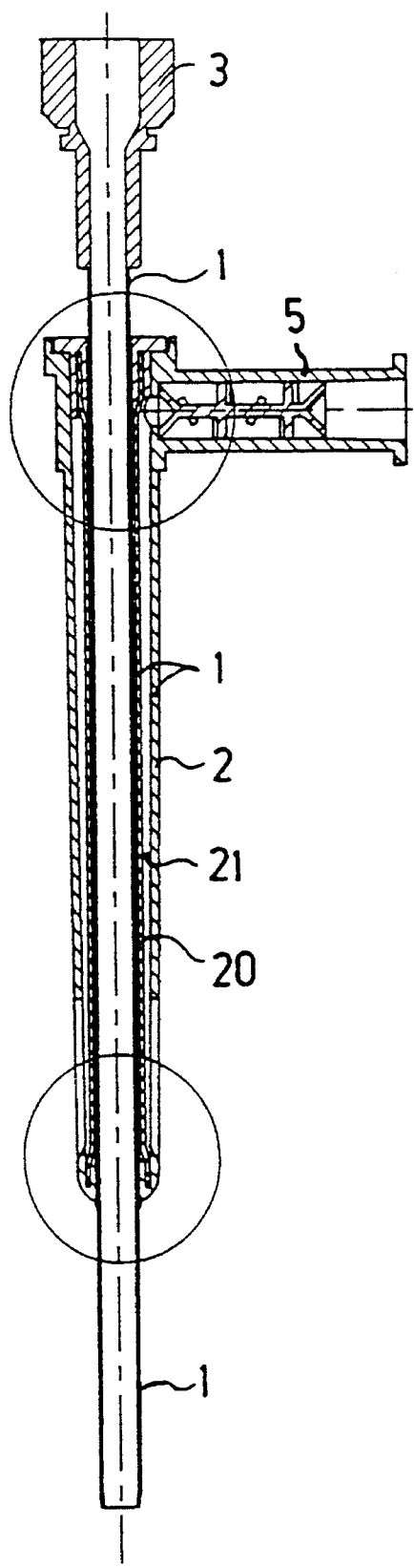
FIG. 8 is a longitudinal cross sectional view through the device of FIG. 6.
Figure 9:
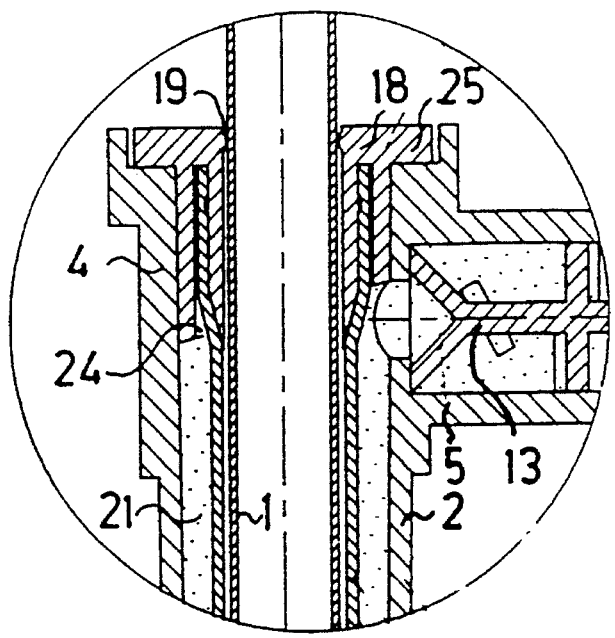
FIG. 9 is an enlarged cross sectional view of the connector area of the device shown in FIG. 8.
Figure 10:
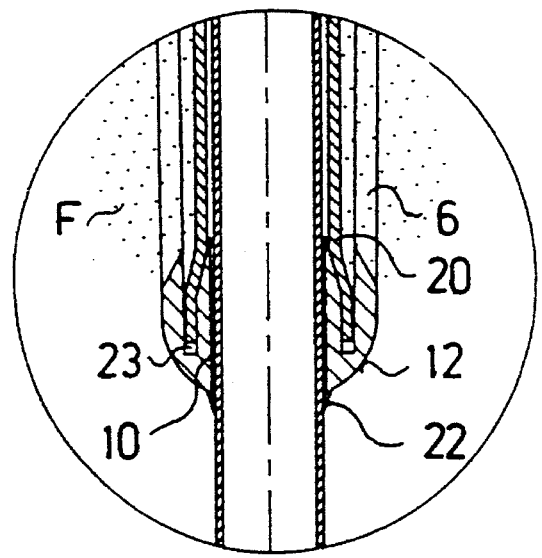
FIG. 10 is a cross sectional view of the exit of the working cannula from the sealing cannula.

The support ribs 9 also result in a stiffening of the also thin-walled sealing cannula 2. As a result, the danger is removed that a slight contraction of the muscular tissue through which the sealing cannula 2 extends could cause a deformation of the sealing cannula 2 which could close the hollow space 7. In this way, the required through-opening for the fibrin sealant is assured in any case. A second preferred embodiment of the device of this invention for introducing two-component fibrin sealant through a puncture channel into the vicinity of an arterial or venous puncture point is shown in FIGS. 6 to 10. While with the first embodiment of this invention discussed hereinabove, the working cannula 1 with the associated medical coupling 3 must be exactly adapted to the sealing cannula for a sealing connection, with this second embodiment, a commercially available working cannula with an arbitrary medical coupling 3 can be used. In this case, a sealing connection between the medical coupling 3 and the sealing cannula 2 not required.

Hardly any difference can be seen in the exterior shape of the two embodiments of the devices of this invention. Accordingly, identical parts have been given the same reference numerals in both embodiments. In accordance with the second embodiment of this invention, the working cannula 1 completely extends in the axial direction through the sealing cannula 2. However, the medical coupling 3 fixedly disposed on the working cannula 1 does not enter the sealing cannula 2, but is located shortly above it. The lower end of the working cannula 1' again is embodied as conical.

The sealing cannula 2 again has a reinforced cuff 4 at its upper end. A connector 5 terminates in the interior of the sealing cannula 2 in the area of the reinforced cuff 4. At its lower end, in the area shortly above the through-opening 10, the sealing cannula 2 also has an outlet opening 6 directed approximately radially outward. In accordance with one embodiment of this invention, several outlet openings 6 are disposed evenly distributed over the circumference, which outlet openings 6 are preferably embodied as slits. The essential difference between this embodiment and the previously described embodiment is seen in particular in the sectional drawing of FIG. 8. In this case, a support envelope 20 is maintained in the sealing cannula 2, which defines a free space 21 between itself and the inner wall of the sealing cannula 2. The working cannula 1 passing through the sealing cannula 2 now extends inside the support envelope 20. The fibrin sealant pressed in through the connector 5 now no longer flows directly between the outer wall of the working cannula 1 and the inner wall of the sealing cannula 2, but instead between the outer wall of the support envelope 20 and the inner wall of the sealing envelope 2. In the area of the lower outlet opening 10, the sealing cannula 2 is provided with a thickened head area 12. This also applies to the first described embodiment. A concentric groove 23 is formed in the inside of the thickened head area 12. This groove 23 narrows from top to bottom, so that the support envelope 20 is slightly widened when it is pushed on and comes to rest sealingly in the annular groove 23. The support envelope 20 is maintained at the top in a similar manner in a lead-in plug 18. The lead-in plug 18 has a centered through-bore 24.

The working cannula 1 enters the support envelope 20 through this bore. An annular sealing bead 25 results in a clamping and sealing support of the working cannula 1 in the support envelope 20. The lead-in plug 18 is provided with a collar 25 which, in the assembled state of the lead-in plug, fits completely into a recess in the reinforced cuff 4. The reinforced cuff 4 in accordance with one preferred embodiment is provided with a reinforced outer diameter in the upper area to provide a sufficient wall thickness. The lead-in plug 18 is also provided with an annular concentric groove 24, whose diameter widens from the bottom to the top, so that the slightly widened support envelope 20 is held clampingly and sealingly. As can be clearly seen from FIG. 9, the two-component fibrin sealant enters the free space 21 through the connector 5 in which the mixing element 13 is disposed.

The head area 12 is preferably abruptly thickened and rounded. The abrupt thickening is used so that the sealing cannula 2 is not pushed through the puncturing place in the blood vessel into the latter. On the other hand, the rounding is intended to ease the introduction of the sealing cannula 2 into the puncture channel.

The working cannula 1 is here also sealed against the sealing cannula 2. This is achieved by a sealing lip 22 at the end, which rests on the outer wall of the working cannula 1.

However, the function of the annular sealing lip 22 in accordance with this embodiment is not the same as that of the sealing bead 11 or the sealing ring of the first embodiment described hereinabove, namely for sealing the hollow space of the sealing envelope 2 and thus preventing the exit of the fibrin sealant in the axial direction, but rather is used for preventing the entry of blood into the area between the working cannula 1 and the support envelope 20.

The employment of the device in accordance with this invention will be briefly described. In a first step, in the course of catheterization, a hollow needle is pushed through the skin and the various tissue layers underneath it up to the blood vessel to be punctured. A guide is pushed into the blood vessel through the hollow needle. Leaving the guide in the introduced position, the hollow needle is retracted over the guide and in place of it a dilator is pushed through the puncture channel into the blood vessel. Afterwards, the working cannula 1 and the sealing cannula 2 are then fed through the dilator, wherein the working cannula 1 is inserted into the blood vessel, while the abruptly thickened head area of the sealing cannula 2 is only pushed in as far as the puncture point. Thus the outlet openings 6 are located above the puncture point of the blood vessel, but inside the puncture channel. The physician now inserts the necessary instruments through the working cannula 1 into the blood vessel. This may be a balloon catheter, a fiber-optical wave guide or the probe of a camera or also other means.

At the end of the operation or examination, first the instruments are pulled out of the vessel through the working cannula 1 and then the two-component fibrin sealant is pressed through the connector 5, the free space 21 or the hollow space 7 and through the outlet openings 6 into the puncture channel. After only a few seconds, the fibrin sealant results in coagulation into a fibrin clot of the blood in the area of the puncture channel or the puncture point, as a result of which bleeding is completely stopped. The formation of hematomas is entirely prevented. A risk of an embolus could no longer be noted. A one hundred percent effectiveness has been achieved in all tests performed to date. No rejection reactions to the human fibrin sealant were noted. Even with the use of an increased concentration of aprotinin, excellent sealing was obtained in animal tests.

Hospitalization of the patient can therefore be omitted.

The use of the human two-component fibrin sealant, known for several years, for use in sealing a puncture point or a puncture channel to the puncture point is not known. This novel sealing method by a fibrin sealant is in no way obvious, because up to now it has always been assumed that the entry of fibrin sealant into the bloodstream could lead to complications. Only the present applicator permits a danger-free use of the fibrin sealant.

The application, in accordance with this invention, of the fibrin sealant can also be done without the device of this invention in that the fibrin sealant is directly applied in the puncture channel by an injection needle. However, because the exact location of the puncture channel by an injection needle is not simple, it is preferred not to employ this method. If the injection of the fibrin sealant takes place outside the area of the puncture channel, there will of course be no sealing of the blood vessel.

Surely other embodiments, besides the above described preferred embodiments of the device in accordance with this invention, are conceivable without departing from the basic concept of this invention.

I claim:

1. In a device for introducing a two-component fibrin sealant into a puncture channel in the vicinity of an arterial or venous puncture point, said device comprising a sealing cannula (2), through which a working cannula, having an open distal end and a proximal end with a fixedly connected medical coupling, extends axially from an upper end through a lower end of said sealing cannula (2), said working cannula movable within said sealing cannula (2) and suitable for conveying intravascular instruments through said working cannula into a vessel, the improvement comprising: the working cannula (1) surrounded at a distance by the sealing cannula (2), whereby the fibrin sealant is conveyed from a connector (5) connected to said upper end of said sealing cannula (2) to at least one slit-shaped radially directed outlet opening (6) in the sealing cannula (2) between the sealing cannula (2) and the working cannula (1); and said sealing cannula (2) comprising a reinforced cuff (4) formed as one piece on an upper end of said sealing cannula (2), an inner diameter of said sealing cannula (2) being reduced from an area of the termination of the connector (5) to the at least one slit-shaped radially directed outlet opening (6).

2. In a device in accordance with claim 1, wherein the connector (5) is laterally integrally formed on the reinforced cuff (4).

3. In a device in accordance with claim 3, wherein a mixing element (13) is insertably maintained in the connector (5).

4. In a device in accordance with claim 1, wherein the connector (5) is a separate piece and is connected to the reinforced cuff (17).

5. In a device in accordance with claim 1, wherein the sealing cannula (2) comprises at least one inwardly oriented support rib (9), thereby maintaining a hollow space (7) for conducting the fibrin sealant (F) from the connector (5) to the at least one outlet opening (6).

6. In a device in accordance with claim 7, wherein the at least one support rib (9) is arranged to extend at least approximately radially.

7. In a device in accordance with claim 1, wherein the working cannula (1) is fixedly connected to a medical coupling (3), said medical coupling (3) maintained in the reinforced cuff (4) of the sealing cannula (2) in one of a frictionally and interlockingly sealing manner and extending axially in respect to the working cannula (1).

8. In a device in accordance with claim 7, wherein in the area of a lower passage (10) of the working cannula (1) through the sealing cannula (2), the sealing cannula (2) comprises a radially inward directed annular sealing bead (11).

9. In a device in accordance with claim 1, wherein the sealing cannula (2) is closed at said upper end by a lead-in plug (18), a tube-shaped support envelope (20) is sealingly maintained within said lead-in plug (18), said robe-shaped support envelope (20) extending through the sealing cannula (2) and sealingly maintained at the opposite lower end in the sealing cannula (2), said working cannula (1) freely movable in the support envelope (20), whereby the fibrin sealant (F) can flow in a radial free space (21) formed between the supporting envelope (20) and the sealing cannula (2) from the connector (5) to said at least one outlet opening (6).

10. In a device in accordance with claim 9, wherein the support envelope (20) comprises a plurality of stiffening ribs (16) directed radially outward and toward an inner wall of the sealing cannula (2).

11. In a device in accordance with claim 1, wherein the sealing cannula (2) comprises an abruptly widened rounded head area (12) at the lower end where the working cannula (1) emerges from the sealing cannula (2).

12. A device in accordance with claim 11, wherein the head area (12) comprises an axially extending annular sealing lip (22) seated on the working cannula (1).

* * * * *